United States Patent

Terrett

Patent Number: 5,482,941
Date of Patent: Jan. 9, 1996

[54] QUINAZOLINONE ANTIANGINAL AGENTS

[75] Inventor: Nicholas K. Terrett, Sandwich, United Kingdom

[73] Assignee: Pfizer Inc., New York, N.Y.

[21] Appl. No.: 232,284
[22] PCT Filed: Nov. 27, 1992
[86] PCT No.: PCT/EP92/02746
§ 371 Date: May 6, 1994
§ 102(e) Date: May 6, 1994
[87] PCT Pub. No.: WO93/12095
PCT Pub. Date: Jun. 24, 1993

[30] Foreign Application Priority Data

Dec. 11, 1991 [GB] United Kingdom ............... 9126260

[51] Int. Cl.$^6$ .............. C07D 239/91; C07D 413/41; A61K 31/505; A61K 31/535
[52] U.S. Cl. .............. 514/253; 514/259; 544/116; 544/284; 544/289
[58] Field of Search .............. 514/253, 259; 544/284, 116, 289

[56] References Cited

U.S. PATENT DOCUMENTS

| | | | |
|---|---|---|---|
| Re. 26,565 | 4/1969 | Rodgers et al. | 260/251 |
| 3,169,129 | 2/1965 | Rodgers et al. | 260/251 |
| 4,159,330 | 6/1979 | Doria et al. | 424/251 |
| 4,379,788 | 4/1983 | Heider et al. | 424/251 |
| 4,431,440 | 2/1984 | Bhalla et al. | 544/289 |
| 5,147,875 | 9/1992 | Coates et al. | 514/259 |
| 5,316,906 | 5/1994 | Haugland et al. | 435/4 |
| 5,426,107 | 6/1995 | Bell et al. | 514/234.2 |

FOREIGN PATENT DOCUMENTS 371731  6/1990  European Pat. Off. .

OTHER PUBLICATIONS

Koizumi, Masuo et al., 4(3H)–Quinazolinones, Chem. Abstracts, 87:201571g (1977).

Primary Examiner—Matthew V. Grumbling
Attorney, Agent, or Firm—Peter C. Richardson; Gregg C. Benson; Robert T. Ronau

[57] ABSTRACT

Compounds of formula:

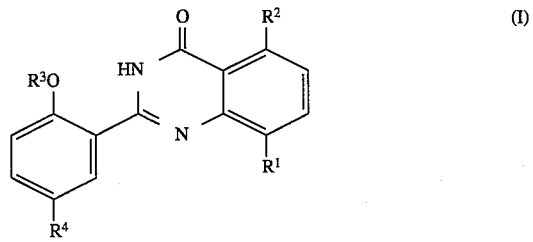

and pharmaceutically acceptable salts thereof
wherein
  $R^1$ is H, $C_1$–$C_4$ alkyl, $C_1$–$C_4$ alkoxy or $CONR^5R^6$;
  $R^2$ is H or- $C_1$–$C_4$ alkyl;
  $R^3$ is $C_2$–$C_4$ alkyl;
  $R^4$ is H, $C_2$–$C_4$ alkanoyl optionally substituted with $NR^7R^8$, (hydroxy)$C_2$–$C_4$ alkyl optionally substituted with $NR^7R^8$, $CH{=}CHCO_2R^9$, $CH{=}CHCONR^7R^8$, $CH_2CH_2CO_2R^9$, $CH_2CH_2CONR^7R^8$, $SO_2NR^7R^8$, $SO_2NH(CH_2)_nNR^7R^8$ or imidazolyl;
  $R^5$ and $R^6$ are each independently H or $C_1$–$C_4$ alkyl;
  $R^7$ and $R^8$ are each independently H or $C_1$–$C_4$ alkyl, or together with the nitrogen atom to which they are attached form a pyrrolidino, piperidino, morpholino or 4-($NR^{10}$)-1-piperazinyl group wherein any of said groups is optionally substituted with $CONR^5R^6$;
  $R^9$ is H or $C_1$–$C_4$ alkyl;
  $R^{10}$ is H, $C_1$–$C_3$ alkyl or (hydroxy)$C_2$–$C_3$ alkyl; and
  n is 2, 3 or 4;
with the proviso that $R^4$ is not H when $R^1$ is H, $C_1$–$C_4$ alkyl or $C_1$–$C_4$ alkoxy; are selective cGMP PDE inhibitors useful in the treatment of cardiovascular disorders such as angina, hypertension, heart failure and atherosclerosis.

6 Claims, No Drawings

QUINAZOLINONE ANTIANGINAL AGENTS

This is a 371 of PCT/EP92/02746 filed Nov. 27, 1992.

This invention relates to a series of quinazolin-4-ones, which are potent and selective inhibitors of cyclic guanosine 3',5'-monophosphate phosphodiesterase (cGMP PDE), having utility in a variety of therapeutic areas including the treatment of cardiovascular disorders such as angina, hypertension, heart failure and atherosclerosis.

The compounds of the invention exhibit selectivity for inhibition of cGMP PDEs rather than cyclic adenosine 3',5'-monophosphate phosphodiesterases (cAMP PDEs) and, as a consequence of this selective PDE inhibition, cGMP levels are elevated, which in turn can give rise to beneficial anti-platelet, anti-neutrophil, anti-vasospastic and vasodilatory activity, as well as potentiation of the effects of endothelium-derived relaxing factor (EDRF) and nitrovasodilators. Thus the compounds have utility in the treatment of a number of disorders, including stable, unstable and variant (Prinzmetal) angina, hypertension, pulmonary hypertension, congestive heart failure, atherosclerosis, conditions of reduced blood vessel patency e.g. post-percutaneous transluminal coronary angioplasty (post-PTCA), peripheral vascular disease, stroke, bronchitis, allergic asthma, chronic asthma, allergic rhinitis, glaucoma, and diseases characterized by disorders of gut motility, e.g. irritable bowel syndrome (IBS).

European patent application EP-A-0371731 discloses a group of quinazolin-4-ones as selective cGMP PDE inhibitors with bronchodilator and vasodilator activity of value in combatting asthma, bronchitis, angina, hypertension and congestive heart failure, but they are less potent as cGMP PDE inhibitors than those compounds hereinafter described.

The compounds of the present invention have the formula (I):

wherein $R^1$ is H, $C_1$–$C_4$ alkyl, $C_1$–$C_4$ alkoxy or $CONR^5R^6$;

$R^2$ is H or $C_1$–$C_4$ alkyl;

$R^3$ is $C_2$–$C_4$ alkyl;

$R^4$ is H, $C_2$–$C_4$ alkanoyl optionally substituted with $NR^7R^8$, (hydroxy)$C_2$–$C_4$ alkyl optionally substituted with $NR^7R^8$, $CH{=}CHCO_2R^9$, $CH{=}CHCONR^7R^8$, $CH_2CH_2CO_2R^9$, $CH_2CH_2CONR^7R^8$, $SO_2NR^7R^8$, $SO_2NH(CH_2)_nNR^7R^8$ or imidazolyl;

$R^5$ and $R^6$ are each independently H or $C_1$–$C_4$ alkyl;

$R^7$ and $R^8$ are each independently H or $C_1$–$C_4$ alkyl, or together with the nitrogen atom to which they are attached form a pyrrolidino, piperidino, morpholino or 4-($NR^{10}$)-1-piperazinyl group wherein any of said groups is optionally substituted with $CONR^5R^6$;

$R^9$ is H or $C_1$–$C_4$ alkyl;

$R^{10}$ is H, $C_1$–$C_3$ alkyl or (hydroxy)$C_1$–$C_3$ alkyl; and n is 2, 3 or 4;

with the proviso that $R^4$ is not H when $R^1$ is H, $C_1$–$C_4$ alkyl or $C_1$–$C_4$ alkoxy; and pharmaceutically acceptable salts thereof.

In the above definition, unless otherwise indicated, alkyl and alkoxy groups having three or more carbon atoms may be straight chain or branched chain.

In addition, alkanoyl groups having four carbon atoms may be straight chain or branched chain.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of formula (I) may also exist in tautomeric forms and the invention includes both mixtures and separate individual tautomers.

Also included in the invention are radiolabelled derivatives of compounds of formula (I) which are suitable for biological studies.

The pharmaceutically acceptable salts of the compounds of formula (I) which contain a basic centre are, for example, non-toxic acid addition salts formed with inorganic acids such as hydrochloric, hydrobromic, sulphuric and phosphoric acid, with organo-carboxylic acids, or with organosulphonic acids. Compounds of formula (I) can also provide pharmaceutically acceptable metal salts, in particular non-toxic alkali metal salts, with bases. Examples include the sodium and potassium salts.

A preferred group of compounds of formula (I) is that wherein $R^1$ is H, methyl, methoxy or $CONR^5R^6$; $R^2$ is H or methyl; $R^3$ is ethyl or n-propyl; $R^4$ is H, acetyl optionally substituted with $NR^7R^8$, hydroxyethyl substituted with $NR^7R^8$, $CH{=}CHCO_2R^9$, $CH{=}CHCONR^7R^8$, $CH_2CH_2CO_2R^9$, $SO_2NR^7R^8$, $SO_2NH(CH_2)_3NR^7R^8$ or 1-imidazolyl; $R^5$ and $R^6$ are each independently H or ethyl; $R^7$ and $R^8$ together with the nitrogen atom to which they are attached form a piperidino, 4-carbamoylpiperidino, morpholino or 4-($NR^{10}$)-1-piperazinyl group; $R^9$ is H or t-butyl; and $R^{10}$ is H, methyl or 2-hydroxyethyl; with the proviso that $R^4$ is not H when $R^1$ is H, methyl or methoxy.

A particularly preferred group of compounds of formula (I) is that wherein $R^1$ is methyl, $CONH_2$ or $CONHCH_2CH_3$; $R^2$ is H; $R^3$ is ethyl or n-propyl; $R^4$ is H, acetyl, 1-hydroxy-2-($NR^7R^8$)ethyl, $CH{=}CHCO_2C(CH_3)_3$, $CH{=}CHCONR^7R^8$, $SO_2NR^7R^8$ or 1-imidazolyl; $R^7$ and $R^8$ together with the nitrogen atom to which they are attached form a 4-($NR^{10}$)-1-piperazinyl group; and $R^{10}$ is methyl or 2-hydroxyethyl; with the proviso that $R^4$ is not H when $R^1$ is methyl.

Especially preferred individual compounds of the invention include:

2-{2-ethoxy-5-[4-(2-hydroxyethyl)-1-piperazinylsulphonyl]pheny}-8-methylquinazolin-4-(3H)-one;

2-{5-[4-(2-hydroxyethyl)-1-piperazinylsulphonyl]-2-n-propoxyphenyl}-8-methylquinazolin-4(3H)-one;

8-methyl-2-{5-[2-(4-methyl-1-piperazinylcarbonyl)ethenyl]-2-n-propoxyphenyl}quinazolin-4(3H)-one;

8-carbamoyl-2-{2-ethoxy-5-[4-(2-hydroxyethyl)-1-piperazinylsulphonyl]phenyl}quinazolin-4(3H)-one; and 8-ethylcarbamoyl-2-(2-n-propoxyphenyl)quinazolin-4(3H)-one.

In another aspect the present invention provides processes for the preparation of compounds of formula (I) and pharmaceutically acceptable salts thereof. Depending on the nature of $R^4$ the compounds of formula (I) may be prepared by a variety of methods from a compound of formula (II):

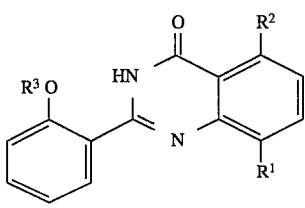

(II)

wherein $R^1$, $R^2$ and $R^3$ are as previously defined For example, when $R^4$ is $C_2$–$C_4$ alkanoyl, the required product is obtainable by conventional Friedel-Crafts acylation whereby (II) is reacted with about a 2-fold excess of an acyl halide of formula ($C_1$–$C_3$ alkyl)COY, wherein Y is halo, preferably chloro or bromo, in the presence of about a 3-fold excess of a Lewis acid such as aluminum chloride or aluminum bromide, in a suitable solvent, e.g. dichloromethane, at from about 0° C. to the reflux temperature of the reaction medium. When $R^4$ is $C_2$–$C_4$ alkanoyl substituted with $NR^7R^8$, wherein $R^7$ and $R^8$ are as previously defined, the product is obtained from (II) via the intermediacy of the corresponding haloketone, i.e. a compound of formula (I) wherein $R^4$ is $CO(C_1$–$C_3$ alkylene) X and X is halo, preferably chloro or bromo, by reaction of the appropriate haloketone with the required amine of formula $R^7R^8NH$ in the presence of at least one equivalent of base to scavenge the liberated acid by-product (HX), in a suitable solvent, e.g. acetonitrile, at about room temperature. The base may be an inorganic salt such as anhydrous potassium carbonate, a tertiary amine such as triethylamine, or excess reactant amine. In cases wherein either $R^7$ or $R^8$ is H, it may be advantageous to use a protected amine of formula $R^7NHP$ or $R^8NHP$ wherein P is a compatible protecting group, e.g. benzyl which can be subsequently removed by catalytic hydrogenation. When both $R^7$ and $R^8$ are H, an ammonia equivalent of formula $P'_2NH$, wherein P' is a protecting group such as t-butoxycarbonyl, may be beneficially employed. In this case, the potassium salt of the non-basic aminating reagent is used for reaction with the haloketone; deprotection is effected by acidolysis using, for example, hydrogen chloride, which allows convenient isolation of the desired aminoketone as its hydrochloric salt. The intermediate haloketone is also obtained via Friedel-Crafts chemistry as described above, in this case between (II) and the appropriate haloacyl halide of formula $X(C_1$–$C_3$ alkylene)COY, wherein X and Y are as previously defined.

Certain aminoketones may be obtained from the parent ketones, i.e. compounds of formula (I) wherein $R^4$ is $C_2$–$C_4$ alkanoyl and $R^1$, $R^2$ and $R^3$ are as previously defined, by α-halogenation (preferably bromination) followed by amination. The bromination may be conducted using a suitably mild brominating reagent such as 1,4-dioxane dibromide in a reaction-inert solvent, e.g. 1,4-dioxane, at the reflux temperature of the reaction medium, whilst the subsequent amination can be effected as described above to afford the corresponding α-aminoketone derivative.

The above ketones of general formula (IA):

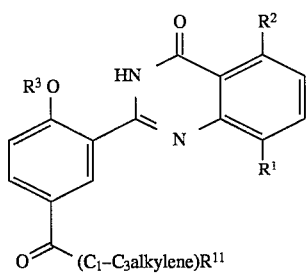

(IA)

wherein $R^{11}$ is either H or $NR^7R^8$, and $R^1$, $R^2$, $R^3$, $R^7$ and $R^8$ are as previously defined, may be reduced to provide the corresponding alcohol derivatives of general formula (IB):

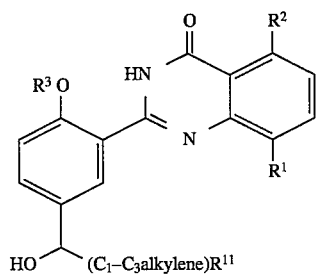

(IB)

wherein $R^1$, $R^2$, $R^3$ and $R^{11}$ are as previously defined The reducing agent is preferably sodium borohydride and the reaction may be conducted in a suitable solvent, e.g. ethanol, at about room temperature.

Compounds of formula (I) wherein is $CH\!=\!CHCONR^7R^8$ or $CH\!=\!CHCO_2R^9$ and $R^1$, $R^2$, $R^3$, $R^7$, $R^8$, and $R^9$, are as previously defined except that $R^9$ is not H, may be Br or I and $R^1$, $R^2$ and $R^3$ are as previously defined, by exploitation of Heck methodology. The required bromo or iodo precursors can be synthesized from a compound of formula (II) using direct bromination or iodination procedures respectively.

For example, the bromo compounds (see formula (III) below) are obtainable by treatment of a compound of formula (II) either with about a 60–100% excess of bromine in glacial acetic acid at about 100° C. or with a similar excess of N-bromosuccinimide in dimethyl-formamide at room temperature. It may be advantageous to use these bromination procedures sequentially, in which event the quantities of reagents can be adjusted as required. The iodination may be effected, for example, using iodine monochloride in glacial acetic acid as solvent.

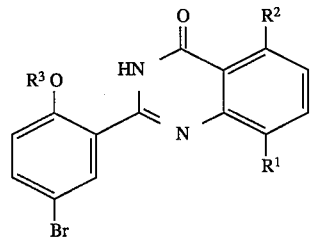

(III)

In the Heck methodology mentioned above, a compound of formula (III), or the corresponding iodo analogue, is reacted with the appropriate acrylic acid amide or ester derivative. The reaction is generally carried out with up to about a 50% excess of the alkene reagent and excess of a tertiary amine such as triethylamine, in the presence of from about 0.1 to 1.0 equivalent of a tertiary arylphosphine, preferably tri-o-tolylphosphine, and about 0.05 to 0.50 equivalent of palladium(II) acetate, in a suitable solvent such as acetonitrile, at the reflux temperature of the reaction medium. The resulting acrylic esters may be hydrolyzed if desired, e.g. using aqueous sodium hydroxide solution, with methanol as co-solvent, to afford the corresponding cinnamic acids. Clearly, these cinnamic acids may be used as an alternative source of cinnamamides of formula (I) wherein $R^4$ is CH=CHCONR$^7$R$^8$ via the corresponding acyl halide (preferably chloride), or other activated acid derivative, by reaction with the appropriate amine of formula HNR$^7$R$^8$. Moreover, all the alkenyl products thus synthesized may be subjected to catalytic hydrogenation, e.g. using 5–10% palladium on charcoal in a suitable solvent at about 15–50 p.s.i. (1.0–3.45 bar) and room temperature, to provide compounds of formula (I) wherein $R^4$ is CH$_2$CH$_2$CONR$^7$R$^8$ or CH$_2$CH$_2$CO$_2$R$^9$ and $R^1$, $R^2$, $R^3$, $R^7$, $R^8$ and $R^9$ are as previously defined for formula (I).

The bromo intermediates of formula (III) are also of utility in the synthesis of compounds of formula (I) wherein $R^4$ is imidazolyl and $R^1$, $R^2$ and $R^3$ are as previously defined. When $R^4$ is C-linked imidazolyl, it may be introduced via palladium-catalyzed coupling of the zincate derivative generated in situ from the corresponding imidazolyllithium intermediate; the latter, in turn, may be obtained from either imidazole or a haloimidazole as necessary by treatment with n-butyllithium. Thus, for example, the imidazolyllithium (in the presence of about 1 extra equivalent of n-butyllithium to accommodate the active hydrogen atom of the quinazolinone substrate) is treated with about 2 equivalents of anhydrous zinc chloride in dry tetrahydrofuran at about −78° C. followed, at about room temperature, by (III) and the palladium catalyst, preferably tetrakis(triphenylphosphine)palladium(O). The reaction mixture can be heated to reflux with addition of up to about 2 further equivalents of anhydrous zinc chloride if necessary. When $R^4$ is N-linked imidazolyl, the reaction may be conducted with up to about a 5-fold excess of imidazole in the presence of about 1 equivalent of base, e.g. anhydrous potassium carbonate, to scavenge the hydrogen bromide by-product, together with about 1 equivalent of copper-bronze and about 0.25 equivalents of iodine catalyst in a suitable solvent, e.g. 1-methyl-2-pyrrolidinone or dimethylformamide, at about the reflux temperature of the reaction medium.

Compounds of the formula (I) wherein $R^4$ is SO$_2$NR$^7$R$^8$ or SO$_2$NH(CH$_2$)$_n$NR$^7$R$^8$ and n are as previously defined may be prepared by the reaction of a compound of formula (IV):

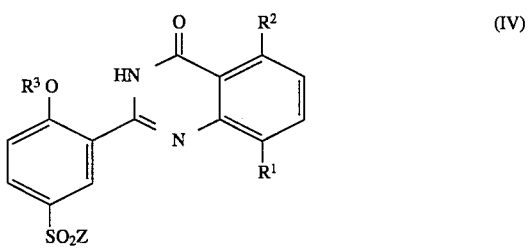
(IV)

wherein $R^1$, $R^2$ and $R^3$ are as previously defined and Z represents a halogen atom, preferably chlorine, with a compound of formula (V) or of formula (VI):

HNR$^7$R$^8$ (V)

H$_2$N(CH$_2$)$_n$NR$^7$R$^8$ (VI)

wherein $R^7$, $R^8$ and n are as previously defined. The reaction is generally carried out at room temperature, preferably in the presence of a solvent, for example a $C_1$–$C_3$ alkanol, using a 2 to 5-fold excess of (V) or (VI) to scavenge the acid by-product (HZ) and, in the case of piperazine ($R^{10}$ is H), also to minimize bis-sulphonamide formation. In the case of reactions involving compounds of formula (VI) wherein either $R^7$ or $R^8$ is H, it may be advantageous to conventionally protect this secondary amino group.

Compounds of formula (IV) are obtainable from compounds of formula (II) by the application of known methods for the introduction of a SO$_2$Z group, wherein Z is as previously defined, into a benzene ring. For example, when Z represents a chlorine atom, by the action of chlorosulfonic acid at or near 0° C.

Compounds of formula (II) may be prepared from compounds of formula (VII):

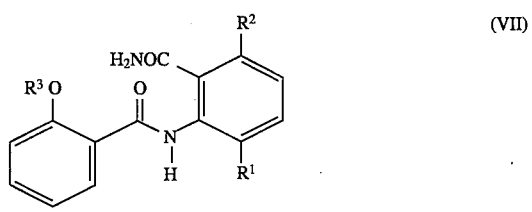
(VII)

wherein $R^1$, $R^2$ and $R^3$ are as previously defined, by the application of known cyclization methods for quinazolinone ring formation. Thus, for example, the cyclization may be effected by the treatment of (VII) with excess of a base such as sodium hydroxide or potassium carbonate, optionally in the presence of excess hydrogen peroxide, in an ethanol-water medium at reflux temperature.

In alternative cyclization procedures, compounds of the formula (II) may be obtained by treatment of (VII) either with polyphosphoric acid at about 140° C. or with anhydrous zinc chloride at about 210° C.

Compounds of formula (VII) may be prepared from compounds of formula (VIII):

(VIII)

wherein $R^1$ and $R^2$ are as previously defined, by reaction with compounds of formula (IX):

(IX)

wherein $R^3$ and Y are as previously defined.

The reaction is generally carried out using from 1 to about 2 equivalents of (IX) in the presence of an excess of a tertiary amine such as triethylamine or pyridine to act as scavenger for the acid by-product (HY), optionally in the presence of a catalyst such as 4-dimethylaminopyridine, in an inert solvent such as dichloromethane, at from about 0° C. to about 25° C. for 2–24 hours. For convenience, pyridine may also be used as solvent.

Compounds of formula (I) may be obtained more directly from a compound of formula (X):

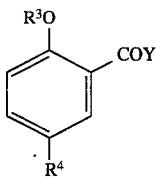

wherein $R^3$, $R^4$ and Y are as previously defined, when such acyl halides are readily accessible, for example when $R^4$ is acetyl as illustrated by Example 22, by reaction with (VIII) and subsequent ring-closure of the product as described above. Clearly this alternative synthetic route will only be appropriate when $R^4$ is compatible with the reaction conditions obtaining in both steps.

Certain of the compounds of formula (I), wherein $R^{10}$ is as previously defined but is not hydrogen, may be prepared directly from the corresponding 4-N-unsubstituted piperazine analogue, i.e. the precursor wherein $R^{10}$ is hydrogen, using appropriate standard alkylation procedures.

The 2-aminobenzamides of formula (VIII), the acyl halides of formulae (IX) and (X), and the intermediates employed for introduction of the various $R^4$ substituents into compounds of formula (II) to afford compounds of formula (I), when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections such that all the compounds defined by formula (I) are obtainable.

The pharmaceutically acceptable acid addition salts of the compounds of formula (I) which contain a basic centre may also be prepared in a conventional manner. For example a solution of the free base is treated with the appropriate acid, either neat or in an appropriate solvent, and the resulting salt isolated either by filtration or by evaporation under vacuum of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The biological activities of the compounds of the present invention were determined by the following test methods.

Phosphodiesterase activity

Compound affinities for cGMP and cAMP PDEs are assessed by determination of their $IC_{50}$ values (the concentration of inhibitor required for 50% inhibition of enzyme activity). The PDE enzymes are isolated from rabbit platelets and rat kidney, essentially by the method of W. J. Thompson et al. (Biochem., 1971, 10, 311). The calcium/calmodulin (Ca/CAM)-independent cGMP PDE and the cGMP-inhibited cAMP PDE enzymes are obtained from rabbit platelets whilst, of the four major PDE enzymes of the rat kidney, the Ca/CAM-dependent cGMP PDE (fraction I) is isolated. Assays are performed using a modification of the "batch" method of W. J. Thompson and M. M. Appleman (Biochem., 1979, 18, 5228). Results from these tests show that the compounds of the present invention are potent and selective inhibitors of Ca/CAM-independent cGMP PDE.

Platelet anti-aggregatory activity

This is assessed by the determination of a compound's ability to inhibit platelet aggregation in vitro induced by platelet activating factor (PAF), and to potentiate the platelet antiaggregatory action in vitro of activators of guanylate cyclase such as nitroprusside and EDRF. Washed platelets are prepared essentially by the method of J. F. Mustard et.al. (Methods in Enzymol., 1989, 169, 3) and aggregation is determined using standard turbidimetric techniques as described by G. V. R. Born, (J. Physiol. (Lond), 1962, 162, 67P).

Antihypertensive activity

This is assessed following intravenous or oral administration of a compound to spontaneously hypertensive rats. Blood pressure is recorded via a cannula implanted in the carotid artery of either conscious or anaesthetised animals.

For administration to man in the curative or prophylactic treatment of the disorders identified on page 1, oral dosages of the compounds will generally be in the range of from 4–800 mg daily for an average adult patient (70 kg). Thus for a typical adult patient, individual tablets or capsules contain from 2–400 mg of active compound, in a suitable pharmaceutically acceptable vehicle or carrier, for administration in single or multiple doses, once or several times per day. Dosages for intravenous, buccal or sublingual administration will typically be within the range of from 1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally, buccally or sublingually, in the form of tablets containing excipients such as starch or lactose, or in capsules or ovules either alone or in admixture with excipients, or in the form of elixirs or suspensions containing flavouring or coloring agents. The compounds may also be injected parenterally, for example intravenously, intramuscularly, subcutaneously or intracoronarily. For parenteral administration, they are best used in the form of a sterile aqueous solution which may contain other substances, for example salts, or monosaccharides such as mannitol or glucose, to make the solution isotonic with blood.

Thus the invention provides a pharmaceutical composition comprising a compound of formula (I), or a pharmaceutically acceptable salt thereof, together with a pharmaceutically acceptable diluent or carrier.

The invention also provides a compound of formula (I), a pharmaceutically acceptable salt thereof, or a pharmaceutical composition containing either entity, for use in medicine.

The invention further provides the use of a compound of formula (I), or a pharmaceutically acceptable salt thereof, or a pharmaceutical composition containing either entity, for the manufacture of a medicament for the treatment of stable, unstable and variant (Prinzmetal) angina, hypertension, pulmonary hypertension, congestive heart failure, atherosclerosis, stroke, peripheral vascular disease, conditions of reduced blood vessel patency e.g. post-PTCA, chronic asthma, bronchitis, allergic asthma, allergic rhinitis, glaucoma, or diseases characterized by disorders of gut motility, e.g. IBS.

In a further aspect, the invention provides a method of treating or preventing stable, unstable and variant (Prinzmetal) angina, hypertension, pulmonary hypertension, congestive heart failure, atherosclerosis, stroke, peripheral vascular disease, conditions of reduced blood vessel patency e.g. post-PTCA, chronic asthma, bronchitis, allergic asthma, allergic rhinitis, glaucoma, or diseases characterized by disorders of gut motility, e.g. IBS, in a mammal (including a human being) which comprises administering to said mammal a therapeutically effective amount of a compound of formula (I), a pharmaceutically acceptable salt thereof, or a pharmaceutical composition containing either entity.

The invention also includes any novel intermediates of formulae (III) and (IV) disclosed herein.

The syntheses of the compounds of the invention and of the intermediates for use therein are illustrated by the following Examples and Preparations. The purity of the compounds was routinely monitored by thin layer chromatography (TLC) using Merck Kieselgel 60 $F_{254}$ plates. $^1$H-Nuclear magnetic resonance (NMR) spectra were recorded using either a Nicolet QE-300 or a Bruker AC-300 spectrometer and were in all cases consistent with the proposed structures.

Room temperature means 20° C. to 25° C.

EXAMPLE 1

2-[2-Ethoxy-5-(1-piperazinylsulphonyl)pheny]- 8-methylquinazolin-4(3H)-one 2-(2-Ethoxyphenyl)-8-methylquinazolin-4(3H)-one (Preparation 4; 2.1 g, 0.0071 mol) was added portionwise to stirred chlorosulfonic acid (15 ml) under a nitrogen atmosphere at 0° C. After 18 hours, the mixture was cautiously added dropwise to stirred ice/water (100 g) and the resulting mixture extracted with dichloromethane-methanol (9:1, 10×100 ml). The organic extracts were combined, dried (MgS$_4$) and evaporated under vacuum. A quantity (1.0 g) of the crude sulphonyl chloride was then added portionwise to a stirred solution of piperazine (2.1 g, 0.0244 mol) in ethanol (30 ml) at room temperature under a nitrogen atmosphere. After 18 hours the mixture was poured into stirred saturated aqueous sodium carbonate solution (100 ml) and the resulting mixture extracted with dichloromethane-methanol (9:1, 10×100 ml). The organic extracts were combined, dried (MgS$_4$) and evaporated under vacuum to give the title compound, which crystallized from ethanol as a colorless solid (0.8 g, 71%), m.p. 163°–165° C. Found: C,56.76; H,5.72; N,11.77. $C_{21}H_4N_4O_5S$; 0.75 $C_2H_5OH$ requires C,56.41; H,6.00; N,11.70%.

EXAMPLE 2

2-{2-Ethoxy-5-[4-(2-hydroxyethyl)-1-piperazinylsulphonyl]phenyl}-8-methylquinazolin-4(3H)-one The title compound was prepared from 2-(2 -ethoxyphenyl)-8-methylquinazolin-4(3H)-one (Preparation 4) and N-(2-hydroxyethyl)piperazine following the procedure of Example 1 and was obtained as a white solid (50%), m.p. 217°–218.5° C. Found: C,56.70; H,5.77; N,11.27. $C_{23}H_{28}N_4O_6S$ requires C,56.54; H,5.78; N,11.47%.

EXAMPLE 3

2-≠2-Ethoxy-5-(1-piperazinylsulphonyl)phenyl]-5-methylquinazolin-4(3H)-one

The title compound was prepared from 2-(2 -ethoxyphenyl)-5-methylquinazol in-4(3H)-one (Preparation 6) and piperazine following the procedure of Example 1 and was obtained as a white solid (42%), m.p. 234°–235° C. Found: C,58.86; H,5.60; N,13.36. $C_{21}H_{24}N_4O_4O$ requires C,58.86; H,5.65; N,13.07%.

EXAMPLE 4

2-{2-Ethoxy-5-[4-(2-hydroxyethyl)-1-piperazinylsulphonyl] phenyl}-5-methylquinazolin-4(3H)-one The title compound was prepared from 2-(2 -ethoxyphenyl)-5-methylquinazolin-4(3H)-one (Preparation 6) and N-(2-hydroxyethyl)piperazine following the procedure of Example 1 and was obtained as a white solid (54%), m.p. 209°–211° C. Found: C,58.58; H,5.85; N,11.62. $C_{23}H_{28}N_4O_4S$ requires C, 58.46; H,5.97; N, 11.86%.

EXAMPLE 5

2-{2-Ethoxy-5-[4-(2-hydroxyethyl)-1-piperazinylsulphonyl]phenyl}-8-methylquinazolin-4(3H)-one The title compound was prepared from 2-(2-ethoxyphenyl)-8-methylquinazolin-4(3H)-one (Preparation 8 ) and N-(2-hydroxyethyl)piperazine following the procedure of Example 1 and was obtained as colorless needles (85%), m.p. 247°–248° C. Found: C,58.12; H,5.86; N,11.88. $C_{23}H_{28}N_4O_5S$ requires C,58.46; H,5.97; N,11.86%.

EXAMPLE 6

2-{5-[4-Hydroxyethyl)-1-piperazinylsulphonyl]2-n-propoxyphenyl}-8-methylquinazolin-4(3H)-one The title compound was prepared from 8-methyl-2-(2-n-propoxyphenyl)quinazolin-4(3H)-one (Preparation 10) and N-(2-hydroxyethyl)piperazine following the procedure of Example 1 and was obtained as colorless needles (84%), m.p. 197°–201° C. Found: C,59.56; H,6.11; N,11.52. $C_{24}H_{30}N_4O_5S$; requires C,59.241 H,6.21; N,11.52%.

EXAMPLE 7

8-Methyl-2-[5-(3-piperidinopropylsulphamoyl)-2-n-propoxyphenyl]quinazolin-4(3H)-one The title compound was prepared from 8-methyl- 2-(2-n-propoxyphenyl)quinazolin-4(3H)-one (Preparation 10) and 3-piperidinopropylamine following the procedure of Example 1 and was obtained as a colorless solid (73%), m.p. 154°–155° C. Found: C, 62.23; H, 6.83; N,11.20. $C_{26}H_{34}N_4O_4S$ requires C,62.62; H,6.87; N,11.24%.

EXAMPLE 8

2-(5-Imidazolyl-2-n-propoxyphenyl)-8-methylquinazolin-4(3H)-one

A stirred mixture of 2-(5-bromo-2-n-propoxyphenyl)-8-methylquinazolin-4(3H)-one (Preparation 11; 0.6 g, 0.0016 mol), anhydrous potassium carbonate (0.22 g, 0.0016 tool), copper bronze (0.1 g, 0.0016 mol), iodine (0.051 g, 0.004 mol), imidazole (0.55 g, 0.008 mol) and 1-methyl-2-pyrrolidinone (20 ml) was heated at 180° C. under a nitrogen atmosphere for 6 hours. The mixture was cooled and poured into water (150 ml), then the resulting mixture extracted with a dichloromethane-methanol mixture (9:1, 4×40 ml ). The organic extracts were combined, dried ($Na_2SO_4$) and evaporated under vacuum. The semi-solid residue was chromatographed on silica gel (10 g) using a methanol in dichloromethane elution gradient (0–4% ). Evaporation of the appropriate fractions gave the title compound which crystallized from ethyl acetate as colorless needles (0.016 g, 3%); Rf 0.5 (silica; dichloromethane-methanol 95:5).

EXAMPLE 9

8-Methyl-2-{5-[2-(4-methyl-1-piperazinylcarbonyl)ethyl]-2-n-propoxyphenyl}quinazolin-4(3H)-one A stirred mixture of 2-(5-bromo-2-n-propoxyphenyl)-8-methylquinazolin-4(3H)-one (Preparation 11; 0.5 g, 0.0013 mol), 1-methyl-4-propenoylpiperazine (Makromol. Chem., 1984, 185, 1525; 0.24 g, 0.0015 mol), palladium diacetate (0.175 g, 0.00077 mol), tri-o-tolylphosphine (0.30 g, 0.001 mol), triethylamine (1 ml) and acetonitrile (25 ml) was heated under reflux under a nitrogen atmosphere for 4 days. The cool mixture was filtered and the filtrate evaporated to dryness under vacuum. The residue was suspended in saturated aqueous sodium carbonate solution (25 ml), the resulting solution extracted with dichloromethane (50 ml) and the organic extract washed with brine (2×30 ml), dried ($Na_2SO_4$) and evaporated under vacuum. Chromatography of the residue on silica gel (10 g), using a methanol in dichloromethane elution gradient (0–4%), gave the title compound which crystallized from hexane-ethyl acetate as a pale pink solid (0.072 g, 12%), m.p. 184°–185° C. Found: C,89.96; H,6.64; N,12.49. $C_{26}H_{30}N_4O_3$ requires C,69.93; N,6.77; N,12.55%.

EXAMPLE 10 t-Butyl 3-(8-methylquinazolin-4(3H)-on-2-yl)-4-n-propoxycinnamate

The title compound was prepared from 2-(5-bromo-2-n-propoxyphenyl)-8-methylquinazolin-4(3H)-one (Preparation 11) and t-butyl acrylate following the procedure of Example 9 and was obtained as colorless crystals (18%), m.p. 196°–197° C. Found: C,71.54; H,6.90; N,6.69. $C_{25}H_{28}N_2O_4$ requires C,71.41; H,6.71; N,6.66%.

EXAMPLE 11

3-(8-Methylquinazolin-4(3H)-on-2-yl)-4-n-propoxycinnamic acid

2N Aqueous sodium hydroxide solution (2.8 ml) was added to a stirred solution of t-butyl 3-(8-methylquinazolin-4(3H)-on-2-yl)-4n-propoxycinnamate (Example 10; 0.79 g, 0.0018 mol) in methanol (2.8 ml) and the resulting solution heated under reflux for 4 hours. The solvent was removed by evaporation under vacuum, the residue-dissolved in water (25 ml) and this solution washed with ethyl acetate (4×30 ml). The aqueous solution was acidified with 2N hydrochloric acid and then extracted with ethyl acetate (3×30 ml). The organic extracts were combined, dried ($Na_2SO_4$) and evaporated under vacuum to give the title compound, which crystallized from ethyl acetate to give a white solid (0.41 g, 60%), m.p. 256°–257° C. Found: C,69.46; H,5.57; N,7.75. $C_{21}H_{20}N_4O_4$ requires C,69.22; H,5.53; N,7.69%.

EXAMPLE 12

3-[3-(8-Methylquinazolin-4(3H)-on-2-yl)-4-4-n-propoxyphenyl]propionic acid

A solution of 3-(8-methylquinazolin-4(3H)-on-2-yl)-4-n-propoxycinnamic acid (Example 11; 0.33 g, 0.00091 mol) in a mixture of ethyl acetate (100 ml), methanol (28.5 ml) and water (1.5 ml), was stirred with palladium on charcoal catalyst under a hydrogen atmosphere at 50 p.s.i. (3.45 bar) for 4 hours. The mixture was then filtered, the filtrate evaporated under vacuum and the residue crystallized from ethyl acetate to give the title compound as an off-white solid (0.224g, 68%), m.p. 215°–216° C. Found: C,68.96; H,6.18; N,7.58. $C_{21}H_{22}N_2O_4$ requires C,68.84; H,6.05; N,7.65%.

EXAMPLE 13

2-{2-Ethoxy-5-[4-(2-hydroxyethyl)-1-piperazinylsulphonyl]phenyl}quinazolin-4(3)-one The title compound was prepared from 2-(2-ethoxyphenyl)quinazolin-4(3H)-one (Japanese Patent Application No. 52 51378) and N-(2-hydroxyethyl)piperazine following the procedure of Example 1 and was obtained as a white solid (78%), m.p. 230°–232° C. Found: C,57.96; H, 5.62; N,12.06. $C_{22}H_{26}N_4O_5S$ requires C,57.63; H,5.72; N,12.22%.

EXAMPLE 14

2-[2-Ethoxy-5-(4-methyl-1-piperazinylsulphonyl)phenyl]quinazolin-4(3H)-one

The title compound was prepared from 2-(2-ethoxyphenyl)quinazolin-4(3H)-one (Japanese Patent Application No. 52 51378) and N-methylpiperazine following the procedure of Example 1 and was obtained as a white solid (79%), m.p. 229°–231° C. Found: C,58.94; H,5.46; N,13.06. $C_{21}H_{24}N_4O_4S$ requires C,58.86; H,5.65; N,13.07%.

EXAMPLE 15

2-[2-Ethoxy-5-(4-carbamoylpiperidinosulphonyl)phenyl]quinazolin-4(3H)-one

The title compound was prepared from 2-(2-ethoxyphenyl)quinazolin-4(3H)-one (Japanese Patent Application No. 52 51378) and 4-carbamoylpiperidine following the procedure of Example 1 and was obtained as a white solid (68%), m.p. 274°–280° C. Found: C,57.90; H,5.45; N,12.26. $C_{22}H_{24}N_4O_5S$ requires C,57.88; H,5.30; N,12.27%.

EXAMPLE 16

2-(2-Ethoxy-5-morpholinoacetylphenyl)-8-methylquinazolin-4(3H)-one

A solution of 1,4-dioxane dibromide (0.5 g, 0.002 mol) in 1,4-dioxane (10 ml) was added dropwise to a stirred solution of 2-(5-acetyl-2-ethoxyphenyl)-8-methylquinazolin-4(3H)-one (Preparation 15; 0.64 g, 0.002 mol) in 1,4-dioxane (40 ml) and the resulting mixture heated under reflux for 2 hours. The precipitate which formed in the cool reaction mixture was collected by filtration, washed with 1,4-dioxane followed by diethyl ether, and air-dried to give 2-(5-bromoacetyl-2-ethoxyphenyl)-8-methylquinazolin-4(3H)-one, which was used without further purification. The crude bromoacetyl intermediate was suspended in stirred acetonitrile (40 ml) and morpholine (0.174 g, 0.002 mol) added; after 1.5 hours at room temperature, the solvent was evaporated under vacuum. The residue was suspended in water (20 ml) and the suspension extracted with dichloromethane (3×20 ml), then the extracts were combined, dried ($Na_2SO_4$) and evaporated under vacuum. The residue was chromatographed on silica gel using a methanol in dichloromethane elution gradient (0–1%) and then the product crystallized from ethyl acetate-hexane to give the title compound as a white powder (0.29 g, 36%), m.p. 172°–173° C. Found: C,68.01; H,6.16; N,10.31. $C_{23}H_{25}N_3O_4$ requires C,67.79; H,6.18; N,10.31%.

EXAMPLE 17

2-[2-Ethoxy-5-(1-hydroxy-2-morpholinoethyl)phenyl]-8-methylquinazolin-4(3H)-one 2-(2-Ethoxy-5-morpholinoacetylphenyl)-8 -methylquinazolin-4(3H)-one (Example 16; 0.2 g, 0.00049 mol) was suspended in stirred ethanol (30 ml) and the mixture treated with sodium borohydride (0.0018 g, 0.00049 mol). After 18 hours at room temperature, the solvent was evaporated under vacuum. The residue was suspended in saturated aqueous sodium carbonate solution (30 ml) and the suspension extracted with ethyl acetate (3×20 ml). The extracts were combined, dried ($Na_2SO_4$) and evaporated under vacuum, then the residue crystallized from ethyl acetate-hexane to give the title compound as colorless plates (0.14 g, 70%), m.p. 145°–147° C. Found: C,67.28; H,6.46; N,10.14. $C_{23}H_{27}3O_4$ requires C,67.46; H,6.65; N,10.26%.

EXAMPLE 18

8-Carbamoyl-2-(2-ethoxyphenyl)quinazolin-4(3H)-one

A stirred mixture of 3-carbamoyl-2-(2-ethoxybenzamido)benzamide (Preparation 18; 1 g, 0,003 mol) sodium hydroxide (0.61 g, 0.015 mol), water (30 ml) and ethanol (7 ml) was heated under reflux for 1 hour. The cool solution was washed with dichloromethane (3×30 ml), acidified to pH 1 with 2N hydrochloric acid and the resulting precipitate collected by filtration. The solid was suspended in saturated aqueous sodium carbonate solution (60 ml) and this suspension extracted with dichloromethane-methanol (98: 2, 3×100 ml). The extracts were combined, dried ($Na_2SO_4$) and evaporated under vacuum, then the residue triturated with diethyl ether (50 ml) to give the title compound as a white solid (0.72 g, 78%), m.p. 252°–254° C. Found: C,66.28; H,4.97; N,13.65. $C_{17}H_{15}H_3O_3$ requires C,66.01; H,4.89; N,13.59%.

EXAMPLE 19

8-Carbamoy-2-{2-ethoxy-5-[4-(2-hydroxyethyl)-1-piperazinylsulphonyl]phenyl} quinazolin-4(3H)-one The title compound was prepared from 8-carbamoyl-2-(2-ethoxyphenyl)quinazolin-4(3H)-one (Example 18) and N-(2-hydroxyethyl)piperazine following the procedure of Example 1 and was obtained as a white hemi-hydrate (12%), m.p. 268°–269° C. Found: C,54.25; H,5.46; N,13.54. $C_{23}H_{27}N_5O_6S$; $0.5\ H_2O$ requires C,54.10; H,5.53; N,13.72%.

EXAMPLE 20

8-Carbamyl-2-(2-n-propoxyphenyl)quinazolin-4(3H)-one 2-n-Propoxybenzoyl chloride (7.27 g, 0.366 mol) was added dropwise to a stirred suspension of 2-amino-3-carbamoylbenzamide (Preparation 17; 2.63 g, 0.0147 mol) in pyridine (50 ml) at 0° C. The mixture was stirred at room temperature for 3 days, then the solvent evaporated under vacuum. The residue was treated with water (100 ml) and, on chilling the solution, colorless crystals formed. The product was collected by filtration and then suspended in a stirred mixture of sodium hydroxide (1.73 g, 0.043 mol), water (90 ml) and ethanol (20 ml). The mixture was heated under reflux for 3 hours, allowed to cool and filtered. The filtrate was acidified to pH 2 with concentrated hydrochloric acid and extracted with a methanoldichloromethane mixture (2:98, 3×100 ml). The organic extracts were combined, washed sequentially with saturated aqueous sodium carbonate solution (3×100 ml) and brine (3×50 ml), dried ($Na_2SO_4$) and evaporated under vacuum. Crystallization of the residue from ethyl acetate-methanol gave the title compound as a white solid (1 g, 40%), m.p. 226°–227° C. Found: C,67.00; H,5.40; N,12.90. $C_{18}H_{17}N_3O_3$ requires C,66.86; H,5.30; N,13.00%.

On standing, the aqueous sodium carbonate washings deposited a precipitate which was collected by filtration. This solid was dissolved in 1N hydrochloric acid (100 ml) and the solution extracted with dichloromethane (3×20 ml). The organic extracts were combined, dried ($Na_2SO_4$) and evaporated under vacuum, then the residue crystallized from ethyl acetate to give 8-carboxy-2-(2-n-propoxyphenyl)quinazolin-4(3H)-one (0.3 g, 11%) as colorless needles, m.p. 195°–197° C. Found: C,66.65; H,5.01; N,8.69. $C_{18}H_{16}N_2O_4$ requires C,66.65; H,4.97; N,8.64.

EXAMPLE 2

8-Ethylcarbamoyl-2-(2-n-propoxyphenyl)quinazolin-4(3H)-one

A solution of oxalyl chloride (0.94 g, 0.0074 mol) in dichloromethane (10 ml) was added dropwise to a stirred solution of 8-carboxy-2-(2-n-propoxyphenyl)quinazolin-4(3H)-one (see Example 20; 1.2 g, 0.0037 mol) in dichloromethane (40 ml) and the resulting mixture stirred for a further 18 hours. The solvent was evaporated under vacuum and the residue triturated with hexane to give the acyl chloride as a yellow solid. This solid was dissolved in dichloromethane (20 ml) and the solution added dropwise to a stirred solution of ethylamine (2.1 g, 0.047 mol) in dichloromethane (40 ml) at 0° C. After 18 hours, the reaction mixture was filtered and evaporated under vacuum. The residue was dissolved in dichloromethane (20 ml) and the solution washed sequentially with 2N hydrochloric acid (3×20 ml), saturated aqueous sodium carbonate solution (3×20 ml) and brine (2×20 ml), then dried ($Na_2SO_4$). Evaporation under vacuum, chromatography of the residue on silica gel (12 g) using a methanol in dichloromethane elution gradient (0–3%), and crystallization of the product from ethyl acetate-hexane gave the title compound as colorless crystals (0.016 g, 1%), m.p. 161°–162° C. Found: C,67.93; H,6.28; N,11.90. $C_{20}H_2N_3O_3$ requires C,68.36; H,6.02; N,11.96%.

EXAMPLE 22

2-(5-Acetyl-2-n-propoxyphenyl)-8-methylquinazolin-4(3H)-one

The title compound was prepared from 2-(5-acetyl-2-n-Propoxybenzamido)-8-methylbenzamide (preparation 21) following the procedure of Example 18 and was obtained as white needles (4%), m.p. 183°–184° C. Found: C,71.37; H,5.86; N,8.32. $C_{20}H_{22}N_2O_4$ requires C,71.41; H,5.99; N,8.33%.

PREPARATION 1

3-Methoxy-2-nitrobenzamide

3-Methoxy-2-nitrobenzoic acid (10.0 g, 0.051 mol) was added portionwise to stirred thionyl chloride (40 ml) and the resulting mixture heated under reflux for 2 hours. The solution obtained was allowed to cool and the solvent evaporated under vacuum. The resulting yellow solid was azeotroped with toluene (2×100 ml) before being dissolved in tetrahydrofuran (100 ml); this solution was added dropwise over 0.5 hour to stirred saturated aqueous ammonia solution (100 ml) at 0° C. After a further 0.25 hour, the mixture was evaporated to dryness under vacuum to give the title compound as a pink solid (9.48 g, 95%), m.p. 212°–214° C. Found: C,49.16; H,4.11; N,13.94. $C_8H_8N_2O_4$ requires C,48.98; H,4.11; N,14.28%

PREPARATION 2

2-Amino-3-methoxybenzamide

3-Methoxy-2-nitrobenzamide (7.0 g, 0.038 mol) was dissolved in ethanol (150 ml) and the solution stirred with Raney nickel catalyst (0.5 g) under a hydrogen atmosphere at 50 p.s.i. (3.45 bar) for 4 hours. The catalyst was removed by filtration and the solvent removed by evaporation under vacuum to give the title compound, after crystallization from ethyl acetatehexane, as a colorless solid (6.3 g, 83%), m.p. 140°–141° C. Found: C,58.03; H,6.06; N,16.65. $C_8H_{10}N_2O_2$ requires C,57.82; H,6.07; N,16.86%.

PREPARATION 3

2-(Ethoxybenzamido-3-methoxybenzamide

2-Ethoxybenzoyl chloride (8.9 g, 0.048 mol) was added dropwise to a stirred solution of 2-amino-3-methoxybenzamide (4.0 g, 0.024 mol) in pyridine (35 ml) under a nitrogen atmosphere at 0° C. After 20 hours at room temperature, the solvent was removed by evaporation under vacuum, the residue dissolved in dichloromethane (100 ml) and the solution washed successively with 2N hydrochloric acid (2×100 ml) and saturated aqueous sodium hydrogen carbonate solution (2×100 ml). The organic phase was dried ($MgSO_4$) and evaporated under vacuum, then the resulting oil chromatographed on silica gel (40 g), eluting with a mixture of methanol in dichloromethane (2%), to give the title compound as a colorless solid (4.1 g, 54%), m.p. 177°–179° C. Found: C,64.97; H,5.83; N,8.74. $C_{17}H_{18}N_2O_4$ requires C,64.96; H, 5.77; N,8.91%.

PREPARATION 4

2-(2-Ethoxyphenyl)-8-methylquinazolin-4(3H)-one

A stirred mixture of 2-(2-ethoxybenzamido)-3-methoxybenzamide (2.6 g, 0.0083 mol), anhydrous potassium carbonate (2.33 g, 0.017 mol), hydrogen peroxide (30%, 4 ml), ethanol (40 ml) and water (80 ml) was heated under reflux for 1 hour. The mixture was allowed to cool and poured into a mixture of water (200 ml) and dichloromethane (100 ml), then the aqueous phase separated, acidified to pH 4 by the addition of 2N hydrochloric acid and extracted with dichloromethane (2×100 ml). The organic solutions were combined, dried ($MgSO_4$) and evaporated under vacuum to give the title compound, which crystallized from ethyl acetate as a colorless solid (2.8 g, 83%), m.p. 198°–199° C. Found: C,68.88; H,5.50; N,9.30. $C_{17}H_{16}N_2O_3$ requires C,68.91; H,5.44; N,9.45%.

PREPARATION 5

2-(2-Ethoxybenzamido)-6-methylbenzamide

A mixture of 2-amino-6-methylbenzamide (UK Patent Application No 1,276,359; 5.49 g, 0.0365 mol), 2-ethoxybenzoyl chloride (7.67 g, 0.0415 mol) and pyridine (100 ml) was stirred at room temperature for 20 hours. The solvent was then removed by evaporation under vacuum and the residue dissolved in dichloromethane (200 ml). The solution was washed with saturated aqueous sodium carbonate solution (200 ml) and the aqueous phase back-extracted with further dichloromethane (2×100 ml). The organic solutions were combined, washed successively with 2N hydrochloric acid (3×100 ml) and brine (100 ml), then dried ($Na_2SO_4$) and evaporated under vacuum to give the title compound, which recrystallized from ethyl acetate as a colorless solid (6.86 g, 63%), m.p. 166°–168° C. Found: C,68.28; H,5.97; N,9.42. $C_{17}H_{18}N_2O_3$ requires C;68.44; H,6.08; N,9.39%.

PREPARATION 6

2-(2-Ethoxyphenyl-5-methylquinazolin-4(3H)-one

The title compound was prepared from 2-(2 -ethoxybenzamido)-6-methylbenzamide following the procedure of Preparation 4 and was obtained as a colorless solid (30%), m.p. 148°–150° C. Found: C,73.08; H,5.83; N,10.03. $C_{17}H_{16}N_2O_2$ requires C,72.84; H,5.75; N,9.99%.

PREPARATION 7

2-(2-Ethoxybenzamido)-3-methylbenzamide

The title compound was prepared from 2-amino-3-methylbenzamide (Chem. Pharm. Bull., 1988, 36, 2955) and 2-ethoxybenzoyl chloride following the procedure of Preparation 5 and was obtained as colorless crystals (71%), m.p. 197°–200° C. Found: C,68.80; H,5.99; N,9.36. $C_{17}H_{18}N_2O_3$ requires C,68.44; H,6.08; N,9.39%.

PREPARATION 8

2-(2-Ethoxyphenyl)-8-methylquinazolin-4(3H)-one

A mixture of 2-(2-ethoxybenzamido)-3-methylbenzamide (1.6 g, 0.0053 mol) and anhydrous zinc chloride (2.29 g, 0.016 mol) was heated at 210° C. for 5 minutes, then allowed to cool. The residue was dissolved in dichloromethane-methanol (90:10, 200 ml) and this solution washed with an aqueous solution of ethylenediamine tetraacetic acid disodium salt (12 g in 400 ml of water). The aqueous phase was then extracted with a mixture of dichloromethane-methanol (90:10, 2×50 ml) and the organic solutions combined, dried ($Na_2SO_4$) and evaporated under vacuum. The residue crystallized from ethanol to give the title compound as colorless needles (0.6 g, 40%), m.p. 177°–180° C. Found: C,72.94; H,5.76; N,9.98. $C_{17}H_{20}N_2O_2$ requires C,72.83; H,5.75; N,10.00%.

PREPARATION 9

3-Methyl-2-(2-n-propoxyphenyl)benzamide

The title compound was prepared from 2-amino-3 -methylbenzamide and 2-n-propoxybenzoyl chloride following the procedure of Preparation 5 and was obtained as a colorless solid (71%), m.p. 140°–142° C. Found: C,69.39; H,6.58; N,8.98. $C_{18}H_{20}N_2O_3$ requires C,69.21; H,6.45; N,8.97%.

PREPARATION 10

8-Methyl-2-(2-n-propoxyphenyl)quinazolin-4(3H)-one

The title compound was prepared from 3-methyl-2-(2-n-propoxybenzamido)benzamide following the procedure of Preparation 4 and was obtained as a colorless solid (77%), m.p. 129°–132° C. Found: C,73.12; H,6.34; N,9.54. $C_{18}H_{18}N_2O_2$ requires C,73.45; H,6.16; N,9.52%.

PREPARATION 11

2-(5-Bromo-2-n-propoxyphenyl)-8-methylquinazolin-4(3H)-one

Bromine (3.2 g, 0.020 mol) was added dropwise to a stirred solution of 8-methyl-2-(2-n-propoxyphenyl)quinazolin- 4(3H)-one (3 g, 0.010 mol) in glacial acetic acid (45 ml) at 95° C. The resulting suspension was heated at 105° C. for 18 hours and then evaporated under vacuum. The resulting solid was dissolved in dimethylformamide (25 ml) and the stirred solution treated dropwise with a solution of N-bromosuccinimide (0.89 g, 0.0051 mol) in dimethylformamide (25 ml). After 1 hour at ambient temperature, the solvent was evaporated under vacuum and the residue dissolved in ethyl acetate (50 ml). This solution was washed with saturated aqueous sodium carbonate solution (50 ml), dried-($Na_2SO_4$)

and evaporated under vacuum. The residue was chromatographed on silica gel (30 g) using a methanol in dichloromethane elution gradient (0–100%) to give the title compound as a white solid (1.67 g, 45%), m.p. 179°–180° C.; Rf 0.7 (silica; dichloromethanemethanol; 99:1). This material was used without any further purification.

PREPARATION 12

Methyl 5-acetyl-2-ethoxybenzoate

A stirred mixture of methyl 5-acetyl-2-hydroxybenzoate (10 g, 0.052 mol), iodoethane (16.4 g, 0.104 mol), anhydrous potassium carbonate (14.4 g, 0.104 mol) and 2-butanone (200 ml) was heated under reflux for 3 days. The solvent was then removed by evaporation under vacuum, the residue dissolved in water (200 ml) and this solution extracted with ethyl acetate (4×200 ml). The organic fractions-were combined, washed with brine (2×200 ml), dried ($Na_2SO_4$) and evaporated under vacuum, then the residue chromatographed on silica gel (130 g) using a methanol in dichloromethane elution gradient (0–1%). Crystallization of the product from ethyl acetate-hexane gave the title compound as colorless crystals (10.15 g, 88%), m.p. 50°–55° C. Found: C,64.88; H,6.38. $C_2H_{14}O_4$ requires C,64.85; H,6.35%.

PREPARATION 13

5-Acetyl-2-ethoxybenzoic acid

A stirred solution of methyl 5-acetyl-2-ethoxybenzoate (9.6 g, 0.043 mol) in a mixture of 1,4-dioxane (80 ml) and water (80 ml) was treated with 5N aqueous sodium hydroxide solution (44 ml, 0.217 mol). The mixture was stirred at room temperature for 18 hours then the solvents evaporated under vacuum. The residue was dissolved in water (100 ml), then this solution was acidified to pH 1 with concentrated hydrochloric acid and extracted with ethyl acetate (4×100 ml). The organic extracts were combined, dried ($Na_2SO_4$) and evaporated under vacuum. Crystallization of the residue from ethyl acetate gave the title compound as a colorless solid (5.4 g, 60%), m.p. 122°–125° C. Found: C,63.20; H,5.81. $C_{11}H_{12}O_4$ requires C,63.45; H,5.81%.

PREPARATION 14

2-(5-Acetyl-ethoxybenzamido)-3-methylbenzamide

Oxalyl chloride (3.66 g, 0.0288 mol) was added dropwise to a stirred solution of 5-acetyl-2-ethoxybenzoic acid (3 g, 0.00144 mol) and dimethylformamide (0.1 ml) in dichloromethane (15 ml). The mixture was stirred at room temperature for 3 hours, then the solvent evaporated under vacuum and the residue azeotroped with hexane (3×50 ml). The crude acyl chloride was dissolved in dichloromethane (20 ml) and the solution added dropwise to a stirred solution of 2-amino-3-methylbenzamide (2.16 g, 0.0144 mol) in pyridine (40 ml) at 0° C. The mixture was allowed to warm to room temperature and stirred for a further 18 hours. The solvent was removed by evaporation under vacuum, the residue dissolved in dichloromethane (50 ml) and this solution then washed with saturated aqueous sodium carbonate solution (50 ml), 2N hydrochloric acid (50 ml) and brine (50 ml), then dried ($Na_2SO_4$) and evaporated under vacuum. Trituration of the residue with diethyl ether gave the title compound as a white solid (2.14 g, 44%), m.p. 214°–216° C. Found: C,66.81; H,5.98; N,8.16. $C_{19}H_{20}N_2O_4$ requires C,67.04; H,5.92; N,8.23%.

PREPARATION 15

2-(5-Acetyl-2-ethoxyphenyl)-methylquinazolin-4-one

The title compound was prepared from 2-(5-acetyl-2-ethoxybenzamido)-3-methylbenzamide following the procedure of Preparation 4 and was obtained as a colorless solid (92%), m.p. 196°–197° C. Found: C,70.97; H,5.69; N,8.66. $C_{19}H_{18}N_2O_3$ requires C,70.79; H,5.63; N,8.75%.

PREPARATION 16

3-Carbamoyl-2-nitrobenzamide

Oxalyl chloride (11.9 g, 0.094 mol) was added dropwise to a stirred solution of 2-nitroisophthalic acid (5 g, 0.0245 mol) and dimethylformamide (0.1 ml) in dichloromethane (100 ml). After 6 hours at room temperature, the solvent was removed by evaporation under vacuum. The residue was triturated with hexane (3×20 ml) and dissolved in tetrahydrofuran (30 ml), then this solution was added dropwise to stirred aqueous ammonium hydroxide solution (30 ml) at 0° C. After 18 hours at room temperature, the mixture was evaporated to dryness under vacuum and water (20 ml) added to the residue. Filtration followed by crystallization of the crude product from a mixture of dimethylformamide-methanol-ethyl acetate gave the title compound as colorless crystals (4 g, 80%), m.p. 283°–285° C. Found C,46.27; H,3.29; N,19.89. requires C,45.94; H,3.37; N,20.09%.

PREPARATION 17

2-Amino-3-carbamoylbenzamide

3-Carbamoyl-2-nitrobenzamide (0.6 g, 0.0029 mol) was dissolved in ethanol (50 ml) and the solution stirred with 5% palladium on charcoal catalyst (0.1 g) under a hydrogen atmosphere at 50 p.s.i. (3.45 bar) and 50° C. for 5 hours. The catalyst was removed by filtration, the solvent evaporated under vacuum and the residue crystallized from water to give the title compound as a grey solid (0.26 g, 50%), m.p.284°–288° C. Found: C,53.49; H,5.00; N,23.31. $C_8H_9N_3O_2$ requires C,53.62; H,5.06; N,23.45%.

PREPARATION 18

3-Carbamoyl-2-(2-ethoxybenzamido)benzamide

The title compound was prepared from 2-amino-3-carbamoylbenzamide and 2-ethoxybenzoyl chloride following the procedure of Preparation 5 and was obtained as colorless crystals (33%), m.p. 224°–225° C. Found: C,62.57; H,5.18; N,12.81. $C_{17}H_{17}N_3O_4$ requires C,62.37; H,5.24; N,12.84%.

PREPARATION 19

Methyl 5-acetyl -2-n-propoxybenzoate

A stirred mixture of methyl 5-acetyl-2-hydroxybenzoate (10 g, 0.0515 mol), 1-iodopropane (10.5 g, 0.0618 mol), anhydrous potassium carbonate (14.2 g, 0.103 mol) and 2-butanone (200 ml) was heated under reflux for 18 hours. A further quantity of 1-iodopropane (10.5 g, 0.0618 mol) was then added and heating under reflux continued for a further 24 hours. The solvent was removed by evaporation under vacuum and the residue partitioned between water (200 ml) and ethyl acetate (200 ml). The aqueous phase was extracted with ethyl acetate (2×100 ml), then the organic solutions combined, dried ($Na_2SO_4$) and evaporated under vacuum. The residue was chromatographed on Silica gel (120 g) using a methanol in dichloromethane elution gradient (0–1%), then crystallization of the product from ethyl acetate-hexane gave the title compound as white crystals (6.85 g, 56%), m.p. 49° C. Found: C,65.76; H,6.72. $C_{13}H_{16}O_4$ requires C,66.08; H,6.83%.

PREPARATION 20

5-Acetyl-2-n-propoxybenzoic acid

The title compound was prepared from methyl 5-acetyl-2-n-propoxybenzoate following the procedure of Preparation 13 and was obtained as colorless crystals (66%), m.p. 104° C. Found: C,64.84; H,6.28. $C_{12}H_{14}O_4$ requires C,64.85; H,6.35%.

PREPARATION 21

2(5-Acetyl-2-n-propoxybenzamido)-8-methylbenzamide

The title compound was prepared from 2-amino-3-methylbenzamide and 5-acetyl-2-n-propoxybenzoyl chloride following the procedure of Preparation 5 and was obtained as white crystals (11%), m.p. 189°–190° C. Found: C,67.63; H,6.40; N,7.85. $C_{20}H_{22}N_2O_4$ requires C,67.78; H,6.26; N,7.90%.

Biological activity.

The following Table illustrates the in vitro activities for a range of the compounds of the invention.

TABLE

IN VITRO PDE INHIBITORY DATA:
SELECTIVITY BETWEEN CALCIUM/CALMODULIN
(Ca/CAM)-INDEPENDENT cGMP PDE AND cGMP-
INHIBITED cAMP PDE

| EXAMPLE | $IC_{50}$ (nM) cGMP | $IC_{50}$ (nM) cAMP | SELECTIVITY RATIO |
|---|---|---|---|
| 5 | 37 | >100,000 | >2,702 |
| 6 | 6.5 | >100,000 | >15,384 |
| 9 | 37 | >100,000 | >2,702 |
| 10 | 54 | >100,000 | >1,851 |
| 17 | 53 | >100,000 | >1,886 |
| 19 | 34 | 67,000 | 1,970 |
| 21 | 14 | >100,000 | >7,142 |
| 22 | 49 | >100,000 | >2,040 |

Safety Profile Examples 4 and 5 have been tested at doses of up to 10 mg/kg i.d. and Example 9 has been tested at doses of up to 1 mg/kg i.d., in rabbit, with no signs of adverse acute toxicity being observed.

I claim:

1. A compound of the formula:

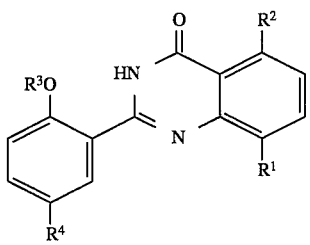

or a pharmaceutically acceptable salt thereof, wherein $R^1$ is H, $C_1$–$C_4$ alkyl, $C_1$–$C_4$ alkoxy or $CONR^5R^6$;

$R^2$ is H or $C_1$–$C_4$ alkyl;

$R^3$ is $C_2$–$C_4$ alkyl;

$R^4$ is H, $C_2$–$C_4$ alkanoyl, (hydroxy) $C_2$–$C_4$ alkyl, CH=CHCO$_2R^9$, CH=CHCONR$^7R^8$, CH$_2$CH$_2$CO$_2R^9$, CH$_2$CH$_2$CONR$^7R^8$, SO$_2NR^7R^8$, SO$_2$NH(CH$_2$)$_n$NR$^7R^8$ or imidazolyl, wherein said $C_2$–$C_4$ alkanoyl and said (hydroxy) $C_2$–$C_4$ alkyl are each independently optionally substituted with $NR^7R^8$;

$R^5$ and $R^6$ are each independently H or $C_1$–$C_4$ alkyl;

$R^7$ and $R^8$ are each independently H or $C_1$–$C_4$ alkyl, or together with the nitrogen atom to which they are attached form a pyrrolidino, piperidino, morpholino or 4-($NR^{10}$)-1-piperazinyl group wherein any of said groups is optionally substituted with $CONR^5R^6$;

$R^9$ is H or $C_1$–$C_4$ alkyl;

$R^{10}$ is H, $C_1$–$C_3$ alkyl or (hydroxy)$C_2$–$C_3$ alkyl;

n is 2, 3 or 4; and with the proviso that $R^4$ is not H when $R^1$ is H, $C_1$–$C_4$ alkyl or $C_1$–$C_4$ alkoxy.

2. A compound as claimed in claim 1 wherein $R^1$ is H, methyl, methoxy or $CONR^5R^6$; $R^2$ is H or methyl; $R^3$ is ethyl or n-propyl; $R^4$ is H, acetyl optionally substituted with $NR^7R^8$, hydroxyethyl substituted with $NR^7R^8$, CH=CHCO$_2R^9$, CH=CHCONR$^7R^8$, CH$_2$CH$_2$CO$_2R^9$, SO$_2NR^7R^8$, SO$_2$NH(CH$_2$)$_3$NR$^7R^8$ or 1-imidazolyl; $R^5$ and $R^6$ are each independently H or ethyl; $R^7$ and $R^8$ together with the nitrogen atom to which they are attached form a piperidino, 4-carbamoylpiperidino, morpholino or 4-($NR^{10}$)-1-piperazinyl group; $R^9$ is H or t-butyl; and $R^{10}$ is H, methyl or 2-hydroxyethyl; with the proviso that $R^4$ is not H when $R^1$ is H, methyl or methoxy.

3. A compound as claimed in claim 2 wherein $R^1$ is methyl, $CONH_2$ or $CONHCH_2CH_3$; $R^2$ is H; $R^3$ is ethyl or n-propyl; $R^4$ is H, acetyl, 1-hydroxy-2-($NR^7R^8$)ethyl, CH=CHCO$_2$C(CH$_3$)$_3$, CH=CHCONR$^7R^8$, SO$_2NR^7R^8$ or 1-imidazolyl; $R^7$ and $R^8$ together with the nitrogen atom to which they are attached form a 4-($NR^{10}$)-1-piperazinyl group; and $R^{10}$ is methyl or 2-hydroxyethyl; with the proviso that $R^4$ is not H when $R^1$ is methyl.

4. A compound as claimed in claim 3 wherein the said compound is selected from

2-{2-ethoxy-5-[4-(2-hydroxyethyl)-1-piperazinylsulphonyl]phenyl}-8-methylquinazolin-4-(3H)-one;

2-{5-[4-(2-hydroxyethyl)-1-piperazinylsulphonyl]-2-n-propoxyphenyl}-8-methylquinazolin-4(3H)-one;

8-methyl-2-{5-[2-(4-methyl-1-piperazinylcarbonyl)ethenyl]-2-n-propoxyphenyl}quinazolin-4(3H)-one;

8-carbamoyl-2-{2-ethoxy-5-[4-(2-hydroxyethyl)-1-piperazinylsulphonyl]phenyl}quinazolin-4(3H)-one; and 8-ethylcarbamoyl-2-(2-n-propoxyphenyl)quinazolin-4(3H)-one;

and pharmaceutically acceptable salts thereof.

5. A pharmaceutical composition comprising a compound according to claim 1 in an amount sufficient to effectively treat stable, unstable and variant angina, hypertension, pulmonary hypertension, congestive heat failure, atherosclerosis, stroke, peripheral vascular disease, conditions of reduced blood vessel patency, chronic asthma, bronchitis, allergic asthma, allergic rhinitis, glaucoma or diseases characterized by disorders of gut motility and a pharmaceutically acceptable diluent or carrier.

6. A method of treating or preventing stable, unstable and variant angina, hypertension, pulmonary hypertension, congestive heart failure, atherosclerosis, stroke, peripheral vascular disease, conditions of reduced blood vessel patency, chronic asthma, bronchitis, allergic asthma, allergic rhinitis, glaucoma or diseases characterized by disorders of gut motility in a mammal, including a human being, comprising administering to said mammal an effective amount of a compound according to claim 1.

* * * * *